United States Patent
D'Onofrio et al.

(10) Patent No.: US 9,675,734 B2
(45) Date of Patent: Jun. 13, 2017

(54) MEDICAL BALLOON COATED WITH THERAPEUTIC AGENT, CARBOXYLIC ACID, AND SALT THEREOF

(71) Applicant: Invatec S.P.A., Roncadelle (Bs) (IT)

(72) Inventors: Simone D'Onofrio, Roncadelle (IT); Federica Bellucci, Roncadelle (IT); Paolo Pellegrini, Roncadelle (IT); Piersandro Pallavicini, Roncadelle (IT)

(73) Assignee: Invatec S.p.a., Roncadelle (IT)

( * ) Notice: Subject to any disclaimer, the term of this patent is extended or adjusted under 35 U.S.C. 154(b) by 167 days.

(21) Appl. No.: 14/472,475

(22) Filed: Aug. 29, 2014

(65) Prior Publication Data

US 2016/0058915 A1   Mar. 3, 2016

(51) Int. Cl.
*A61L 29/08* (2006.01)
*A61L 29/16* (2006.01)
*A61M 25/10* (2013.01)

(52) U.S. Cl.
CPC ............... *A61L 29/08* (2013.01); *A61L 29/16* (2013.01); *A61M 25/10* (2013.01); *A61M 25/104* (2013.01); *A61L 2300/21* (2013.01); *A61L 2300/216* (2013.01); *A61L 2300/22* (2013.01); *A61L 2300/416* (2013.01); *A61L 2300/606* (2013.01); *A61L 2300/802* (2013.01); *A61L 2420/02* (2013.01); *A61L 2420/06* (2013.01); *A61M 2025/105* (2013.01)

(58) Field of Classification Search
None
See application file for complete search history.

(56) References Cited

U.S. PATENT DOCUMENTS

| 7,750,041 | B2 | 7/2010 | Speck et al. |
| 8,257,305 | B2 | 9/2012 | Speck et al. |
| 2008/0118544 | A1 | 5/2008 | Wang |
| 2008/0255509 | A1 | 10/2008 | Wang |

FOREIGN PATENT DOCUMENTS

| WO | WO2009/018816 | 2/2009 |
| WO | WO2009/140257 | 11/2009 |
| WO | WO2013/091722 | 6/2013 |
| WO | WO2013/092416 | 6/2013 |
| WO | WO2014/143048 | 9/2014 |

OTHER PUBLICATIONS

PCT/US2015/046384, "The International Search Report and the Written Opinion of the International Searching Authority" mailed Nov. 23, 2015, 11pgs.

*Primary Examiner* — Robert A Wax
*Assistant Examiner* — Randeep Singh

(57) ABSTRACT

A coated medical balloon that includes a polymeric material having a surface with a therapeutic agent-containing mixture coated thereon, wherein the mixture includes a therapeutic agent, an unsaturated carboxylic acid, and a salt of the unsaturated carboxylic acid.

24 Claims, 6 Drawing Sheets

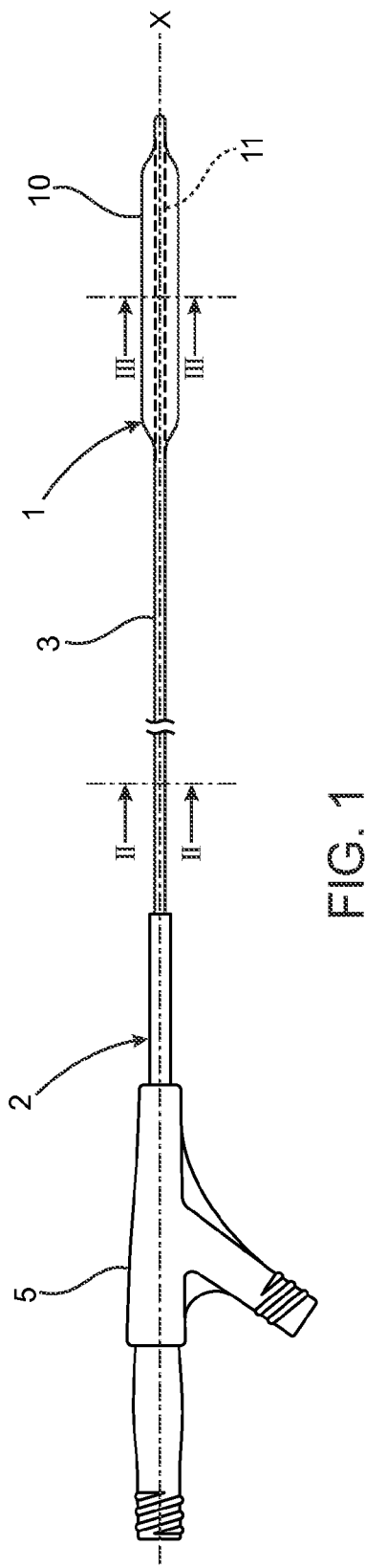
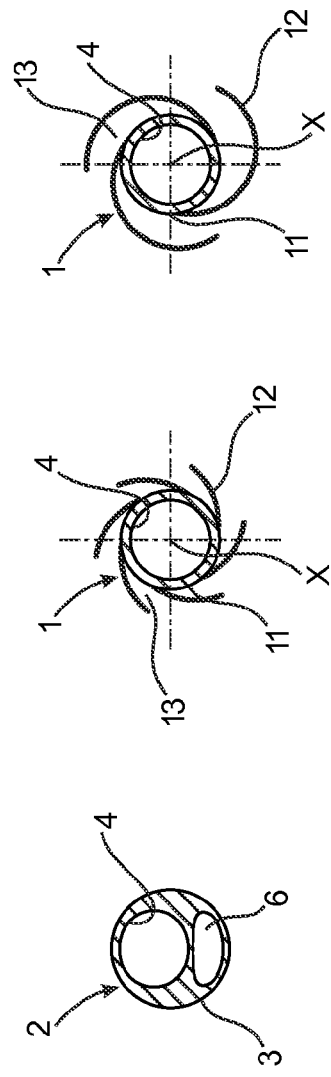

MEDICAL BALLOON COATED WITH THERAPEUTIC AGENT, CARBOXYLIC ACID, AND SALT THEREOF

BACKGROUND

Using targeted delivery, a controlled dose of a therapeutic agent may be delivered directly to a target site, e.g., a lesion in a diseased vessel, while avoiding or minimizing exposing other healthy parts of the body to the agent. Also, thanks to a local (targeted) delivery, greater amounts of therapeutic agent may be delivered to the afflicted parts of the body. In one approach to localized delivery, a balloon catheter is used, wherein the balloon has therapeutic agent disposed on its outer surface and is expanded within a vessel to deliver the therapeutic agent to the vessel wall at the lesion site to be treated. There is still a need for improved balloon catheter devices for delivery of one or more therapeutic agents to an intravascular site.

SUMMARY

The present disclosure provides medical balloons that include a surface with a therapeutic agent-containing mixture coated thereon, wherein the mixture includes a therapeutic agent, an unsaturated carboxylic acid, and a salt of the unsaturated carboxylic acid.

In one embodiment of the present disclosure, there is provided a coated medical balloon (made of a polymeric material) having a surface with a therapeutic agent-containing mixture coated thereon, wherein the mixture includes a therapeutic agent, an unsaturated carboxylic acid, an alkali metal salt of the unsaturated carboxylic acid, and an optional excipient.

In another embodiment of the present disclosure, there is provided a coated medical balloon (made of a polymeric material) having a therapeutic agent-containing mixture coated thereon, wherein the mixture includes a therapeutic agent, an unsaturated carboxylic acid, a salt of the unsaturated carboxylic acid, and an optional excipient, wherein the ratio of acid to salt is within a range (which includes the endpoints) of 80:20 to 20:80, or in some embodiments 60:40 to 40:60. In another embodiment of the present disclosure, there is provided a balloon catheter that includes: an elongated catheter shaft having proximal and distal ends, wherein the catheter shaft defines a longitudinal axis extending between the proximal and distal ends; and an inflatable balloon located close to the distal end of the catheter shaft, wherein the balloon (made of a polymeric material) has a surface with a therapeutic agent-containing mixture coated thereon, wherein the mixture includes a therapeutic agent, an unsaturated carboxylic acid, an alkali metal salt of the unsaturated carboxylic acid, and an optional excipient.

In another embodiment of the present disclosure, there is provided a balloon catheter that includes: an elongated catheter shaft having proximal and distal ends, wherein the catheter shaft defines a longitudinal axis extending between the proximal and distal ends; and an inflatable balloon located close to the distal end of the catheter shaft, wherein the balloon (made of a polymeric material) has a surface with a therapeutic agent-containing mixture coated thereon, wherein the mixture includes a therapeutic agent, an unsaturated carboxylic acid, a salt of the unsaturated carboxylic acid, and an optional excipient, wherein the ratio of acid to salt is within a range (which includes the endpoints) of 80:20 to 20:80, or in some embodiments 60:40 to 40:60. The balloons of the present disclosure were engineered to exert their therapeutic action within the time of contact between the balloon surface and the vessel wall, thus they can be considered "therapeutic agent-transferring-devices."

The present disclosure also provides methods of making and methods of using the disclosed medical balloons and balloon catheters of the present disclosure.

In one embodiment of using the balloon catheter of the present disclosure, there is provided a method of delivering a therapeutic agent to a diseased vessel, the method including: providing a balloon catheter as described herein; advancing the balloon catheter into the diseased vessel; and inflating the inflatable balloon to form an inflated balloon that contacts the wall of the diseased vessel and thereby delivers the therapeutic agent from the surface of the inflated balloon to the diseased vessel.

In one embodiment of making, there is provided a method of reducing the amount of therapeutic agent on a coated balloon, the method including: providing a medical balloon having a surface; combining components that include a therapeutic agent, an unsaturated carboxylic acid, a salt of the unsaturated carboxylic acid, and an optional excipient to form a mixture; and coating the mixture onto the surface of the medical balloon.

In another embodiment of making, there is provided a method of reducing the amount of therapeutic agent on a coated balloon, the method including: providing a medical balloon having a surface; combining components that include a therapeutic agent, an oleic acid, an alkali metal salt of the oleic acid, and an optional excipient to form a mixture, wherein the ratio of acid to salt is within a range (which includes the endpoints) of 80:20 to 20:80 (or in some embodiments 60:40 to 40:60); and coating the mixture onto the surface of the medical balloon.

The terms "distal" and "proximal" are used in the following description with respect to a position or direction relative to the treating clinician. "Distal" or "distally" refer to a position distant from or in a direction away from the clinician. "Proximal" and "proximally" refer to a position near or in a direction toward the clinician.

Herein, "located close to the distal end of the catheter shaft" means located closer to the distal end of the catheter shaft than the proximal end of the catheter shaft. Preferably, in certain embodiments "located close to the distal end of the catheter shaft" means located at the ultimate distal end of the catheter shaft.

The terms "polymer" and "polymeric material" (including elastomer and elastomeric polymer) include, but are not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiotactic, and atactic symmetries.

The term "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration.

The terms "a," "an," and "the" are used interchangeably with the term "at least one."

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise. The term "and/or" means one or all of the listed elements or a combination of any two or more of the listed elements.

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used.

Also herein, the recitations of numerical ranges by endpoints include all numbers subsumed within that range as well as the endpoints (e.g., 1 to 5 includes 1, 1.5, 2, 2.75, 3, 3.80, 4, 5, etc.). Herein, "up to" a number (e.g., up to 50) includes the number (e.g., 50).

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list.

DRAWINGS

The disclosure may be more completely understood in connection with the following drawings.

FIG. 1 is a side view of an angioplasty balloon catheter with the balloon in its unexpanded configuration.

FIG. 2 is the cross-section along the line II-II in FIG. 1.

FIG. 3A is a possible cross-section along the line III-III in FIG. 1.

FIG. 3B is another possible cross-section along the line III-III in FIG. 1.

DETAILED DESCRIPTION OF ILLUSTRATIVE EMBODIMENTS

Figure 4:
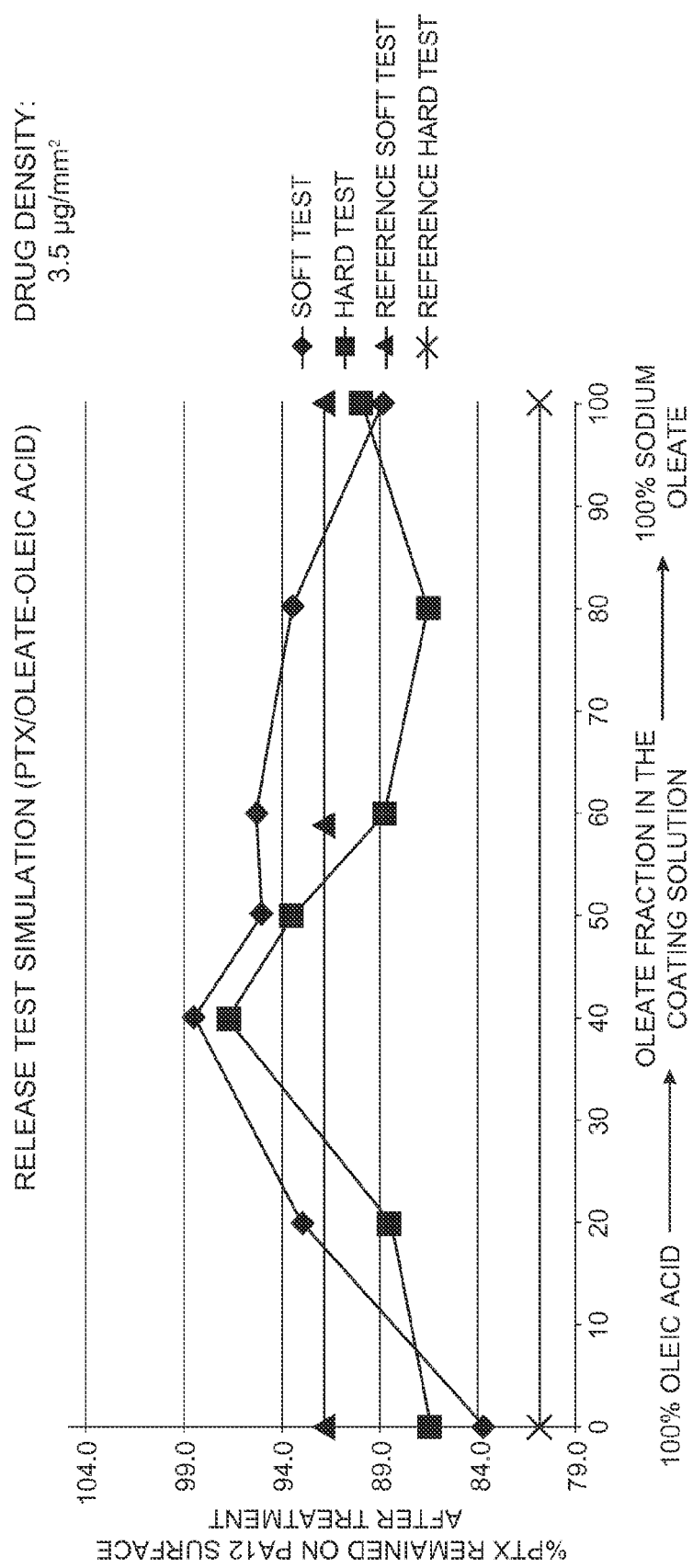
FIG. 4 is a graphical representation of the Soft and Hard Release Simulation Test results of a reference coating solution compared with a coating solution of the present disclosure containing 40% oleic acid and 60% sodium oleate (Coating 5) coated at a paclitaxel density of 3.5 g/mm$^2$.

The present disclosure relates to medical balloons and balloon catheters. The medical balloons according to the present disclosure have a surface with a therapeutic agent-containing mixture coated thereon, wherein the mixture includes a therapeutic agent, an unsaturated carboxylic acid, and a salt of the unsaturated carboxylic acid. In certain embodiments, the balloon catheter can also include an optional elastomeric sheath positioned on at least said balloon surface, wherein each of the balloon and the elastomeric sheath have a surface with a therapeutic agent-containing mixture coated thereon, wherein the mixture includes a therapeutic agent, an unsaturated carboxylic acid, and a salt of the unsaturated carboxylic acid.

Medical Balloons and Balloon Catheters

The medical balloons of the present disclosure have a surface with a therapeutic agent-containing mixture coated thereon. The mixture includes one or more therapeutic agents, one or more unsaturated carboxylic acids, and one or more salts of the unsaturated carboxylic acid. The balloon can be any of a wide variety of medical balloons made of one or more polymeric materials.

With reference to the figures, in FIG. 1 there is an exemplary angioplasty balloon 1 that is mounted at the distal end of an angioplasty balloon catheter 2. The catheter 2 further includes an elongated tubular body 3 that is provided with a plurality of lumens 4, 6 (see FIG. 2), and of a connector 5 at the proximal end of tubular body 3. The balloon 1 is suitable to alternatively adopt a deployed configuration and a collapsed configuration. The balloon may be brought to the deployed configuration by means of the injection of a pressurized inflating liquid. The balloon may be brought to the collapsed configuration by means of the suction of the inflating liquid. The balloon is suitable, in the collapsed configuration, to be inserted within the circulatory system of a patient's body and to be advanced along the vessels to reach a diseased vessel section, e.g. affected by stenosis or restenosis. The balloon 1 is further suitable to apply, when it passes from the collapsed configuration to the deployed configuration, a radial force to the diseased area such as to expand the latter and restore the nominal section of the vessel. The balloon 1 comprises an outer wall 10 (FIG. 1) that, in the unexpanded state, is wrapped in a plurality of laps 12 (FIG. 3A and FIG. 3B) around a core 11 that defines the distal end of catheter 2 (i.e., a guide wire tube which comprises a lumen 4 suitable for receiving a guide wire). The core 11 defines an axis X (FIG. 3A and FIG. 3B) about which the balloon 1 is developed. In certain embodiments, each of the laps 12 is laid such as to provide a cavity 13 between each lap and the core 11. Cavities 13 are suitable for being filled with a therapeutic agent coating solution. Lumen 6 is suitable for receiving an inflating fluid which is used for expanding the balloon.

Thus, the present disclosure provides a balloon catheter that includes: an elongated catheter shaft having a proximal end and a distal end, wherein the catheter shaft defines a longitudinal axis extending between the proximal end and the distal end; an inflatable balloon (typically, in a folded state) located close to the distal end of the catheter shaft (i.e., closer to the distal end of the catheter shaft than the proximal end of the catheter shaft). The balloon includes a surface with a therapeutic agent-containing mixture coated thereon, wherein the mixture includes a therapeutic agent, an unsaturated carboxylic acid, a salt of the unsaturated carboxylic acid, and an optional excipient.

Optionally, the balloon catheter may also include an elastomeric sheath (not shown) having a surface with a therapeutic agent-containing mixture coated thereon, wherein the mixture includes a therapeutic agent, an unsaturated carboxylic acid, and a salt of the unsaturated carboxylic acid. The balloon and the optional sheath may include the same or different therapeutic agents disposed thereon (as a result of the therapeutic agent being coated on the surface or impregnated into the elastomeric material). Herein, an elastomeric material is a polymeric material that resembles rubber because it generally resumes its original shape when a deforming force is removed. An exemplary material for the elastomeric sheath is polytetrafluoroethylene (PTFE). The elastomeric sheath may be made of a variety of other elastomeric materials, such as polyamides, polyurethanes, polyvinyl chloride, blends, copolymers, and multi-layered combinations thereof.

In certain embodiments of the present disclosure, although not shown in the figures, the balloon catheter may include an optional protective sheath positioned around the balloon or, if present, around the elastomeric sheath that is positioned around the balloon. The wall thickness of the protective sheath may be 0.001 inch, for example, or thicker. The protective sheath may be made of the same material as the elastomeric sheath, although this is not a requirement. The protective sheath may be made of a variety of other polymeric materials, such as polyethylene (PE) and high density polyethylene (HDPE). Blends, copolymers, and multi-layered combinations of such materials may be used in the protective sheath.

The balloon 1 of the balloon catheter shown in the figures may be any of a variety of conventional balloons for use in balloon catheters. They may be of any of a variety of lengths, diameters, thicknesses, etc., as is needed for the particular use. The balloon may be made of a compliant, semi-compliant, or non-compliant material. Semi-compliant and non-compliant balloons are most useful for peripheral indications. An exemplary material for the balloon is any of a wide variety of grades of nylon (e.g., nylon-12). The balloon may be made of a variety of other conventional polymeric materials, such as polyethylene terephthalate (PET), polyethylene (PE), high density polyethylene (HDPE), polyamide copolymers, polyurethanes, polyvinyl chloride, blends, copolymers, and multi-layered combinations thereof.

Therapeutic Agents

The therapeutic agent may be any of a variety of therapeutic agents. Typically, these include agents for treating heart disease, various cardiovascular ailments, and other vascular conditions, including blockages, occlusions, stenoses or diseased regions in the coronary artery, femoral artery, peripheral arteries, and other arteries or even veins in the body. Treatment of vascular conditions may include the prevention or correction of various ailments and deficiencies associated with the cardiovascular system, the cerebrovascular system, urinogenital systems, biliary conduits, abdominal passageways and other biological vessels within the body. Preferred therapeutic agents are those capable of producing a beneficial effect against one or more conditions including coronary restenosis, cardiovascular restenosis, angiographic restenosis, arteriosclerosis, hyperplasia, and other diseases or conditions. For example, the therapeutic agent may be selected to inhibit or prevent vascular restenosis, a condition corresponding to a narrowing or constriction of the diameter of the bodily lumen typically due to a stent deployment or to a balloon angioplasty procedure. An antirestenotic drug such as rapamycin, a rapamycin analogue, or a rapamycin derivative may be used to prevent or reduce the recurrence or narrowing and blockage of the bodily vessel. Another preferred therapeutic agent is the antirestenotic Taxanes, particularly paclitaxel.

The amount of the therapeutic agent applied to the balloon (and optionally to the elastomeric sheath, if present) may vary depending on the characteristics of the particular agent or combination of agents. Generally, the dose of therapeutic agent disposed on a balloon of the present disclosure is of at least 1 microgram per square millimeter (1 $\mu g/mm^2$). Typically the therapeutic agent is coated to achieve a total amount disposed on the surface of the balloon in a range from about 1 $\mu g/mm^2$ to about 5 $\mu g/mm^2$.

The therapeutic agent may be disposed on, and preferably adhered to, the balloon with or without the use of any binding agents, e.g., polymeric binders. If binding agents are used, examples of such agents include, for example, urea, azides, gels, biodegradable/bioabsorbable polymers. Various combinations of therapeutic agents may be used if desired.

Carboxylic Acids and Salts Thereof

Therapeutic agent-containing mixtures coated on medical balloons of the present disclosure include a therapeutic agent, an unsaturated carboxylic acid (particularly one with a hydrophobic moiety), and a (corresponding) salt of the unsaturated carboxylic acid.

In certain embodiments, the unsaturated carboxylic acid is selected from the group of fatty acids having a (C6-C20) carbon chain with a single cis C=C bond. Examples of such carboxylic acids include oleic acid, vaccenic acid, sapienic acid, palmitoleic acid, and myristoleic acid. In certain embodiments, the unsaturated carboxylic acid is oleic acid.

In certain embodiments, the salt of the unsaturated carboxylic acid is an alkali metal salt, or an alkaline earth metal salt. In certain embodiments, the salt is a sodium salt.

In certain embodiments, the weight molar ratio of unsaturated carboxylic acid to salt thereof is within a range (inclusive of the endpoints) of 80:20 to 20:80. In certain embodiments, the weight molar ratio of unsaturated carboxylic acid to salt thereof is within a range (inclusive of the endpoints) of 60:40 to 40:60. In certain embodiments, the weight molar ratio of unsaturated carboxylic acid to salt thereof is 50:50.

While not intending to be bound by theory, it is believed that the unsaturated carboxylic acids described herein have a favorable chemical affinity with a cell membrane and can find a suitable and effective way for penetrating inside a cell membrane. This penetration action inside a cell membrane, and the relevant perturbation associated therewith, is believed to be particularly desirable because it creates an important obstacle to the cell membrane proliferation and growth, this particular effect favorably supporting the therapeutic agent activity that is directed to avoiding cell proliferation.

Surprisingly, in certain embodiments of the unsaturated carboxylic acids of the present disclosure, the double bond's cis-configuration is believed to advantageously perturb the cell membrane to a greater extent than the analogous trans-configuration. While not intending to be bound by theory, it is believed that, although a trans-configuration is characterized by a linear chain that can penetrate the cell membrane, due to its straight disposition it does not cause a substantial modification of the structure thereof. In contrast, the cis-configuration has a curved (arcuate) structure that is believed to penetrate the cell membrane and induce a considerably high perturbation in the cell membrane. Such a high degree of perturbation is believed to be particularly advantageous for certain therapeutic agents (e.g., paclitaxel—referred to herein as "Tx" or "PTX"), as both contribute to favorably decreasing the cell membrane proliferation. Also, surprisingly, in certain embodiments, the amphiphilic characteristics possessed by the salts of the unsaturated carboxylic acids of the present disclosure are particularly advantageous for improving the release of the therapeutic agent at the site to be treated (e.g., a stenosis or restenosis) as well as the uptake of the therapeutic agent at the treated site. For example, the carboxylate group can provide a suitable interaction with the alcohol, ester, and/or the amide substituents of a therapeutic agent (e.g., paclitaxel), while the hydrophobic moiety of the carboxylic acids can suitably interact with the hydrophobic component of the therapeutic agent. Although not wishing to be bound by theory, it is believed that such interactions due to such amphiphilic characteristics of the carboxylic acids lead to the formation of crystals of the therapeutic agent (e.g., paclitaxel) of very small size. Such crystals of small size are believed to be desirable for one or more of the following reasons: (1) crystals of limited size can be taken up more easily by the vessel wall; (2) the risk of the small crystals being washed out after the balloon is expanded is reduced; and (3) the size and the amount of the particulate generated from the coating are considerably decreased during delivering of the balloon catheter to the lesion site, as well as during balloon expansion for releasing the therapeutic agent to the diseased tissue. Applicant discovered that the therapeutic agent-containing mixture according to the present disclosure remarkably improves the efficacy of a coated medical device. In particular, the present disclosure may provide one or more of the following advances over the state of the art of coated medical balloons: (1) it reduces the particulate amount and the particulate size (which is typically lower than 10 micrometers ($\mu$m)) (and possibly even the formation of particulate) formed and detached from the coated balloon surface during delivering of the balloon catheter to the lesion site and during balloon expansion; (2) it increases the amount of therapeutic agent that reaches the lesion site and that is available for being delivered to the vessel wall (since the amount of therapeutic agent lost during travelling to the lesion site is reduced); (3) it provides a reliable and reproducible coating process which advantageously contributes in manufacturing a uniform and homogeneous coating on the balloon surface; (4) it contributes to enhancement of therapeutic agent efficacy at the cellular level (e.g., it provides for a very effective grafting to the vessel wall and a very effective attack to the cells (i.e. opening the cellular bridges) for a better uptake of the therapeutic agent into the cellular membranes).

Optional Excipients

In some embodiments of the present disclosure, the therapeutic agent-containing mixture may include at least one excipient. Suitable excipients include ascorbic acid, urea, polyethylene glycol (e.g., PEG 8000) and a triglyceride (e.g., a triglyceride that is solid at room temperature, such as trimyristin). In some embodiments, the excipient is urea.

Methods of Making

The therapeutic agent mixed with an unsaturated carboxylic acid and salt thereof may be applied to the balloon using a variety of coating or impregnating techniques. Balloons can be coated with a therapeutic agent (e.g., drug) coating solution, mixed with an unsaturated carboxylic acid and salt thereof, by application techniques such as dipping, spraying, painting, brushing, pipeting, and by using a syringe (e.g., U.S. Pat. No. 8,257,305 and U.S. Pat. No. 7,750,041; and International Pub. No. WO 2009/018816).

In many of the current balloon coating methods, a coating solution that includes at least one therapeutic agent, an unsaturated carboxylic acid, a salt thereof, an optional excipient, and a solvent is applied to a balloon to form a substantially uniform layer of therapeutic agent. The concentration of the therapeutic agent applied to the balloon of the present disclosure varies depending on the therapeutic agent intended use. The solvent is typically selected from water, tetrahydrofuran, ethanol, or a combination thereof. The solvent amount can range from 7 to 300 microliters ($\mu$l) depending on the size of the balloon surface to be coated.

Methods of Use

In one embodiment of the present disclosure, there is provided a method of delivering one or more therapeutic agents to a diseased vessel.

In an exemplary general method, the method includes: providing a balloon catheter as described herein; advancing the balloon catheter into the diseased vessel while the balloon is in its folded condition; inflating the inflatable balloon to form an inflated balloon that contacts the wall of the diseased vessel and thereby delivers a therapeutic agent from the surface of the inflated balloon to a site of the diseased vessel; deflating the inflated balloon to reform the inflatable balloon into a reformed (folded) balloon; and removing the balloon catheter from the diseased vessel.

In an exemplary general method wherein the balloon catheter also includes an elastomeric sheath positioned onto the coated balloon, the method includes: providing a balloon catheter as described herein; advancing the balloon catheter into the diseased vessel; inflating the inflatable balloon to form an inflated balloon and an expanded sheath, the latter contacting the wall of the diseased vessel and thereby delivering a therapeutic agent from the surface of the expanded sheath to a first site of the diseased vessel; deflating the inflated balloon to reform the inflatable balloon into a reformed inflatable balloon; removing the elastomeric sheath from around the reformed inflatable balloon; and inflating the reformed inflatable balloon (after removing the elastomeric sheath) to contact the wall of the diseased vessel to deliver a therapeutic agent from the surface of the inflated balloon to the first site, or to a different site of the same or a different diseased vessel if the reformed inflatable balloon is moved to a different site after the expanded sheath contacts the wall of the diseased vessel and before inflating the reformed inflatable balloon.

In certain preferred methods, the balloon catheter further includes a protective sheath positioned around the elastomeric sheath and the inflatable balloon located in the elastomeric sheath, and the method further includes removing the protective sheath after advancing the balloon catheter into the diseased vessel.

Exemplary Embodiments

Embodiment 1 is a coated medical balloon comprising a polymeric material having a surface with a therapeutic agent-containing mixture coated thereon, wherein the mixture comprises (or consists essentially of, or consists of) a therapeutic agent, an unsaturated carboxylic acid, an alkali metal salt of the unsaturated carboxylic acid, and an optional excipient.

Embodiment 2 is the balloon of embodiment 1 wherein the unsaturated carboxylic acid is selected from the group of fatty acids having a (C6-C20) carbon chain with a single cis C═C bond.

Embodiment 3 is the balloon of embodiment 2 wherein the unsaturated carboxylic acid is oleic acid.

Embodiment 4 is the balloon of any one of embodiments 1 through 3 wherein the alkali metal salt is a sodium salt.

Embodiment 5 is the balloon of any one of embodiments 1 through 4 wherein the ratio of acid to salt is within a range of 80:20 to 20:80.

Embodiment 6 is the balloon of claim 5 wherein the ratio of acid to salt is within a range of 60:40 to 40:60.

Embodiment 7 is the balloon of any one of embodiments 1 through 6 wherein the therapeutic agent is a Taxane.

Embodiment 8 is the balloon of embodiment 7 wherein the Taxane is paclitaxel.

Embodiment 9 is a coated medical balloon comprising a surface having a therapeutic agent-containing mixture coated thereon, wherein the mixture comprises (or consists essentially of, or consists of) a therapeutic agent, an unsaturated carboxylic acid, a salt of the unsaturated carboxylic acid, and an optional excipient, wherein the ratio of acid to salt is within a range of 60:40 to 40:60.

Embodiment 10 is the balloon of embodiment 9 wherein the unsaturated carboxylic acid is selected from the group of fatty acids having a (C6-C20) carbon chain with a single cis C═C bond.

Embodiment 11 is the balloon of embodiment 10 wherein the unsaturated carboxylic acid is oleic acid.

Embodiment 12 is the balloon of any one of embodiments 9 through 11 wherein the salt is an alkali metal salt.

Embodiment 13 is the balloon of embodiment 12 wherein the alkali metal salt is a sodium salt.

Embodiment 14 is the balloon of any one of embodiments 9 through 13 wherein the therapeutic agent is a Taxane.

Embodiment 15 is the balloon of embodiment 14 wherein the Taxane is paclitaxel.

Embodiment 16 is the balloon of any one of embodiments 1 through 15, wherein the therapeutic agent-containing mixture further comprises an excipient.

Embodiment 17 is the balloon of embodiment 16 wherein the excipient is selected from the group of: ascorbic acid, urea, polyethylene glycol (e.g., PEG 8000) and a triglyceride (in particular triglycerides that are solid at room temperature, such as trimyristin).

Embodiment 18 is a balloon catheter comprising: an elongated catheter shaft having proximal and distal ends, wherein the catheter shaft defines a longitudinal axis extending between the proximal and distal ends; and an inflatable balloon located close to the distal end of the catheter shaft, wherein the balloon comprises a polymeric material having a surface with a therapeutic agent-containing mixture coated thereon, wherein the mixture comprises (or consists essentially of, or consists of) a therapeutic agent, an unsaturated carboxylic acid, an alkali metal salt of the unsaturated carboxylic acid, and an optional excipient.

Embodiment 19 is the balloon catheter of embodiment 18 wherein the unsaturated carboxylic acid is selected from the group of fatty acids having a (C6-C20) carbon chain with a single cis C═C bond.

Embodiment 20 is the balloon catheter of embodiment 19 wherein the unsaturated carboxylic acid is oleic acid.

Embodiment 21 is the balloon catheter of any one of embodiments 18 through 20 wherein the alkali metal salt is a sodium salt.

Embodiment 22 is the balloon catheter of any one of embodiments 18 through 21 wherein the therapeutic agent is a Taxane.

Embodiment 23 is the balloon catheter of embodiment 22 wherein the Taxane is paclitaxel.

Embodiment 24 is the balloon catheter of any one of embodiments 18 through 23 wherein the ratio of acid to alkali metal salt is within a range of 80:20 to 20:80.

Embodiment 25 is the balloon catheter of embodiment 24 wherein the ratio of acid to salt is within a range of 60:40 to 40:60.

Embodiment 26 is a balloon catheter comprising: an elongated catheter shaft having proximal and distal ends, wherein the catheter shaft defines a longitudinal axis extending between the proximal and distal ends; and an inflatable balloon located close to the distal end of the catheter shaft, wherein the balloon comprises a polymeric material having a surface with a therapeutic agent-containing mixture coated thereon, wherein the mixture comprises (or consists essentially of, or consists of) a therapeutic agent, an unsaturated carboxylic acid, a salt of the unsaturated carboxylic acid, and an optional excipient, wherein the ratio of acid to salt is within a range of 60:40 to 40:60.

Embodiment 27 is the balloon catheter of embodiment 26 wherein the unsaturated carboxylic acid is selected from the group of fatty acids having a (C6-C20) carbon chain with a single cis C═C bond.

Embodiment 28 is the balloon catheter of embodiment 27 wherein the unsaturated carboxylic acid is oleic acid.

Embodiment 29 is the balloon catheter of any one of embodiments 26 through 28 wherein the salt is an alkali metal salt.

Embodiment 30 is the balloon catheter of embodiment 29 wherein the alkali metal salt is a sodium salt.

Embodiment 31 is the balloon catheter of any one of embodiments 26 through 30 wherein the therapeutic agent is a Taxane.

Embodiment 32 is the balloon catheter of embodiment 31 wherein the Taxane is paclitaxel.

Embodiment 33 is the balloon catheter of any one of embodiments 18 through 32, wherein the therapeutic agent-containing mixture further comprises an excipient.

Embodiment 34 is the balloon catheter of embodiment 33 wherein the excipient is selected from the group of: ascorbic acid, urea, polyethylene glycol (e.g., PEG 8000) and a triglyceride (in particular triglycerides that are solid at room temperature, such as trimyristin).

Embodiment 35 is a method of delivering a therapeutic agent to a diseased vessel, the method including: providing a balloon catheter of any one of embodiments 18 through 34;

advancing the balloon catheter into the diseased vessel; and inflating the inflatable balloon to form an inflated balloon that contacts the wall of the diseased vessel and thereby delivers the therapeutic agent from the surface of the inflated balloon to the diseased vessel.

Embodiment 36 is a method of reducing the amount of therapeutic agent on a coated balloon, the method comprising: providing a medical balloon comprising a polymeric material having a surface; combining components comprising (or consists essentially of, or consists of) a therapeutic agent with an unsaturated carboxylic acid, a salt of the unsaturated carboxylic acid, and an optional excipient to form a mixture; and coating the mixture onto the surface of the medical balloon.

Embodiment 37 is the method of embodiment 36 wherein the unsaturated carboxylic acid is selected from the group of fatty acids having a (C6-C20) carbon chain with a single cis C=C bond.

Embodiment 38 is the method of embodiment 37 wherein the unsaturated carboxylic acid is oleic acid.

Embodiment 39 is the method of any one of embodiments 36 through 38 wherein the salt is an alkali metal salt.

Embodiment 40 is the method of embodiment 39 wherein the alkali metal salt is a sodium salt.

Embodiment 41 is the method of any one of embodiments 36 through 40 wherein the ratio of acid to salt is within a range of 80:20 to 20:80.

Embodiment 42 is the method of embodiment 41 wherein the ratio of acid to salt is within a range of 60:40 to 40:60.

Embodiment 43 is the method of any one of embodiments 36 through 42 wherein the therapeutic agent is a Taxane.

Embodiment 44 is the method of embodiment 43 wherein the Taxane is paclitaxel.

Embodiment 45 is the method of any one of embodiments 36 through 44 wherein the mixture comprises a solvent selected from water, tetrahydrofuran, ethanol, or a combination thereof.

Embodiment 46 is the method of embodiment 45 wherein the solvent is present in an amount of 7-300 µl.

Embodiment 47 is the method of embodiment 45 or 46 further comprising removing the solvent.

Embodiment 48 is the method of any one of embodiments 36 through 47, wherein the therapeutic agent-containing mixture further comprises an excipient.

Embodiment 49 is the method of embodiment 48 wherein the excipient is selected from the group of: ascorbic acid, urea, polyethylene glycol (e.g., PEG 8000) and a triglyceride (in particular triglycerides that are solid at room temperature, such as trimyristin).

Embodiment 50 is a method of reducing the amount of therapeutic agent on a coated balloon, the method comprising: providing a medical balloon comprising a polymeric material having a surface; combining components comprising (or consists essentially of, or consists of) a therapeutic agent with an oleic acid, an alkali metal salt of oleic acid, and an optional excipient to form a mixture, wherein the ratio of acid to salt is within a range of 60:40 to 40:60; and coating the mixture onto the surface of the medical balloon.

Embodiment 51 is the method of embodiment 50 wherein the alkali metal salt is a sodium salt.

Test Methods Description

Soft Release Test

For simulating the behavior of a balloon catheter while tracking through a blood vessel, a "Soft Release" test was set up. The coating solution was applied with a syringe on the surface of a Polyamide 12 plate sample (having dimensions 2 cm×1 cm). The solvent was allowed to evaporate and then the coated plate was dipped into 30 ml of distillate water and shaken with a Reciprocating Stirrer at 40 rpm for 15 minutes. The concentration of PTX released from the coated plate and present in the distillate water was successively determined with a UV spectrophotometer (in the wavelength range of 200-400 nm, the PTX maximum absorbance was at 228 nm) and the concentration of PTX remained on the coated plate was thus calculated. Since the plate surface as well as the desired density of therapeutic agent to be applied were known, the volume of coating solution to be prepared could be easily calculated.

Hard Release Test

For simulating the behavior of a balloon catheter during inflation/deflation of the balloon in a blood vessel and thus evaluating the amount of therapeutic agent that is released from the coated balloon as a consequence of the mechanical force exerted on the coated balloon during inflation/deflation thereof, a "Hard Release" test was set up. The coating solution was applied with a syringe on the surface of a Polyamide 12 plate sample (having dimensions 2 cm×1 cm). The solvent was allowed to evaporate and then the coated plate was dipped into 30 ml of distillate water in an Ultrasonic Bath, 35 kHz, for 5 minutes. The concentration of PTX released from the coated plate and present in the distillate water was successively determined with a UV spectrophotometer (in the wavelength range of 200-400 nm, the PTX maximum absorbance was at 228 nm) and the concentration of PTX remained on the coated plate was thus calculated. Since the plate surface as well as the desired density of therapeutic agent to be applied were known, the volume of coating solution to be prepared could be easily calculated.

MTT Test

This test is a colorimetric assay for assessing cell viability. NAD(P)H-dependent cellular oxidoreductase enzymes are key enzymes in the Krebs cycle. Evaluation of this enzyme by biochemical means is commonly used to check cellular health and viability. Such enzymes are capable of reducing the tetrazolium dye MTT, which is 3-(4,5-dimethylthiazol-2-yl)-2,5-diphenyltetrazolium bromide (successively referred to as MTT Solution), to its insoluble formazan, which has a purple color. This test allows to measure the succinate dehydrogenase (SDH) activity of cells.

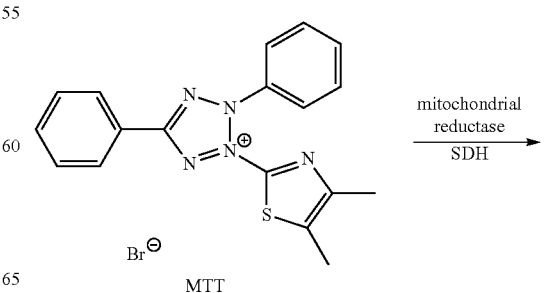

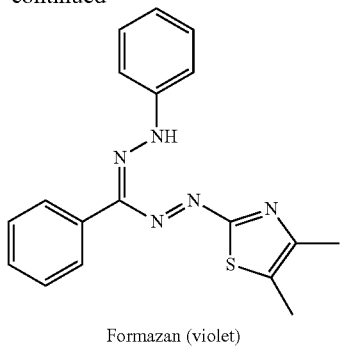

Formazan (violet)

In-Vitro Coating Efficacy Evaluation Test

A cell culture medium (produced by Gibco, Invetrogen, Milan, Italy) was used consisting of: Essential Minimum Eagle's Medium with L-glutamine (MEM GlutaMAX), 10% fetal bovine serum, streptomycin (100 micrograms per liter (μg/L)), penicillin (100 Units per mililiter (U/ml)).

The cell culture medium (contained in a 250 ml culture flask) was cultured at 37° C. in a humidified incubator equilibrated with 5% $CO_2$. Fibroblasts were harvested from the culture flask prior to confluence (i.e. prior to starting the cellular proliferation) by means of a sterile trypsin-EDTA solution (0.05 trypsin, 0.02% EDTA in normal Dulbecco's Phophate Buffered Saline (DPBS), pH 7.4), then resuspended in the cell culture medium, and diluted to $1 \times 10^5$ cells/ml. Four milliliters (4 ml) of the cell suspension were seeded into each well of 6-well polystyrene Petri dishes (3.5 cm diameter FALCON dishes). Experiments were started when cells reached about 80% confluence, by visual inspection.

The coated samples (to be contacted with the cell suspension contained in the Petri dishes) were prepared by applying through a micropipette a defined volume of different coating solutions (as shown in the following of the present description) onto the surface of plates or balloon strips made from Polyamide 12 and having dimensions of 2 cm×1 cm.

The apparatus for performing the test comprised: a support for positioning the Petri dishes containing the cell suspension, a clamp for accommodating a coated sample to be tested, and a guide holder that carried the clamp and was able to be vertically translated so that the coated sample could be completely immersed into the cell suspension contained in the wells of the Petri dishes.

Each coated sample was immersed into one single well for 60 seconds. During this contact time, the PTX was transferred to the cell suspension. Immediately after the contact between the coated sample and the cell suspension was completed, the sample was removed from the well and the culture medium was aspirated, and new medium was added. This step guarantees that each and every effect on cell growth is actually due only to the therapeutic agent directly transferred to the cell wall during the contact time, and not to some other therapeutic agent eventually detached from the sample coating, but remained in the culture medium and only at a later time (greater than the contact time) possibly come into contact with the cells wall.

This in-vitro test was performed to reasonably and realistically mimic the therapeutic agent transfer that occurs from a Drug Coated Balloon Catheter to the cells membrane at the lesion site when the balloon is expanded and its coated surface comes into contact with the vessel wall. This method was designed to evaluate the efficacy of the therapeutic agent transfer process as well as the different behaviour of various coating solutions.

The cells were placed in an incubator and cell growth was followed for a 72-hour time span. At 72 hours, representative images of cell morphology were obtained using a LEICA DM14000B inverted microscope equipped with an epifluorescence system.

Finally, at 72 hours the MTT Test was performed to evaluate the biosynthetic activity of the cell layers. Therefore, the cells were washed with sterile DPBS, and successively the DPBS was replaced with 3 ml/well of MTT sodium succinate solution (5 mg/ml solution). The cells and the MTT solution were incubated at 37° C. for 3 hours in the incubator. During this time, the MTT solution was transformed by the cells' mitochondrial dehydrogenase into insoluble Formazan. Therefore, the amount of produced Formazan is measured by spectrophotometric analysis, and from this amount it is possible to measure the mitochondrial activity, and thus the cell viability. A high concentration of Formazan corresponds to a high absorbance, high cell viability, and low efficacy of the coating. In contrast, a low concentration of Formazan corresponds to a low absorbance, low cell viability, and high efficacy of the coating.

At the end of the incubation period, the MTT solution was removed and replaced with 2 ml/well of dimethylsulfoxide. The wells were then swirled for 5 minutes until the purple color was uniform. The absorbance was evaluated at a wavelength of 560 nm.

In each 6-well microplate typically three wells were filled with the same coating solution to be tested and the remaining three wells were used as blank control, i.e. the cells were cultured without any contact with the coated samples. Therefore, three values of absorbance were obtained for each tested coating solution (one value of absorbance for each well) and three values of absorbance were obtained for the three blank controls.

Examples

Preparation of the Coating Solutions

For simulating the behavior of the coated balloons according to the present disclosure, the following coating solutions were prepared:
1) PTX+100% Oleic Acid (coating 1: comparative)
2) PTX+80% Oleic Acid/20% Sodium Oleate (coating 2)
3) PTX+60% Oleic Acid/40% Sodium Oleate (coating 3)
4) PTX+50% Oleic Acid/50% Sodium Oleate (coating 4)
5) PTX+40% Oleic Acid/60% Sodium Oleate (coating 5)
6) PTX+20% Oleic Acid/80% Sodium Oleate (coating 6)
7) PTX+100% Sodium Oleate (coating 7: comparative)
8) coating solution comprising PTX (coating 8: competitor's product—reference)

By using a micropipette the above coating solutions have been applied on the surface of a Polyamide 12 sample having dimensions 2 cm×1 cm in order to obtain a predetermined PTX density (3.5 μg/mm², 2.8 μg/mm² and 2.1 μg/mm² as better explained in the following of the present disclosure).

Exemplary Preparation Method—Preparation of the coating solution: PTX+40% Oleic Acid/60% Sodium Oleate (Coating 5)

A correct preparation of the coating solution required a two-step process to be performed. A first solution (solution 1) was prepared comprising 28 mg of PTX dissolved in 500 μl of THF (tetrahydrofuran) (THF of >99.5% purity). A second solution (solution 2) was prepared comprising 20 μl of oleic acid dissolved in 175 μl of ethanol and 80 μl of Sodium hydroxide 0.454 M. The final coating solution (coating 5) was obtained by mixing solution 1 and 50 μl of solution 2.

The other coating solutions listed above (specifically, coatings 2, 3, 4 and 6) were prepared by using the same preparation method.

Soft and Hard Release Simulation Test Results

The Soft and Hard Release Tests described above were carried out on the coating solutions of the present disclosure as well as on the reference coating solution and the coating solutions 1 and 7 at a PTX density of 3.5 μg/mm$^2$. A coating solution amount of about 14 μl was used to obtain this PTX density. The results are shown in Table 1 and FIG. 4.

TABLE 1

Coatings (PTX density of 3.5 μg/mm$^2$)

| Test | Soft Release | Hard Release |
|---|---|---|
| Coatings | % of PTX remained on PA12 surface after treatment | % of PTX remained on PA12 surface after treatment |
| Coating 1 | 83.7 (stdv.: 5.6) | 86.4 (stdv.: 5.0) |
| Coating 2 | 93.0 (stdv.: 5.0) | 88.3 (stdv.: 8.9) |
| Coating 3 | 98.4 (stdv.: 3.4) | 96.7 (stdv.: 3.7) |
| Coating 4 | 95.0 (stdv.: 5.9) | 93.4 (stdv.: 7.5) |
| Coating 5 | 95.2 (stdv.: 4.2) | 88.7 (stdv.: 3.3) |
| Coating 6 | 93.5 (stdv.: 4.4) | 86.5 (stdv.: 2.4) |
| Coating 7 | 88.8 (stdv.: 4.0) | 89.9 (stdv.: 1.5) |
| Coating 8 (reference) | 91.9 (stdv.: 1.70) | 80.8 (stdv: 6.50) |

The results reported in Table 1 show a remarkable improvement of the coating solutions of the present disclosure with respect to the coating solution (reference) known in the art. In particular, since the Soft Release Test was designed to evaluate the behavior of a coated balloon during tracking of the balloon catheter within the blood vessel to the lesion site, it is apparent that high percentages of therapeutic agent still remained coated on the balloon surface are preferred because this means that a low therapeutic agent percentage is lost during delivery of the balloon catheter to the lesion to be treated. The data in Table 1 show that the values of the coating solutions of the present disclosure (coatings 2, 3, 4, 5, and 6) are higher than the values of the reference coating and of the coatings 1 and 7.

Furthermore, since the Hard Release Test was designed to evaluate the behavior of a coated balloon during inflation/deflation thereof (in order to estimate the amount of therapeutic agent that is lost in the blood flow when the mechanical forces correlated to balloon inflation/deflation occur, this therapeutic agent amount being thus no more available to be up-taken by the vessel wall when the latter is contacted by the expanded balloon), it is apparent that high percentages of therapeutic agent still remained coated on the balloon surface are preferred because this means that a low therapeutic agent percentage is lost due to mechanical expansion/deflation of the coated balloon. The data in Table 1 show that the values of the coating solutions of the present disclosure (coatings 2, 3, 4, 5, and 6) are higher than the values of the reference coating and of the coatings 1 and 7.

The Soft and Hard Release Tests were also carried out on the coating 5 at a PTX density of 2.8 μg/mm$^2$ and 2.1 μg/mm$^2$. The results are shown in Tables 2 and 3.

TABLE 2

Coating 5 (PTX density of 2.8 μg/mm$^2$)

| | Soft Release | Hard Release |
|---|---|---|
| % of PTX remained on PA12 surface after treatment | 97.38 (stdv.: 4.97) | 87.58 (stdv.: 7.03) |

TABLE 3

Coating 5 (PTX density of 2.1 μg/mm$^2$)

| | Soft Release | Hard Release |
|---|---|---|
| % of PTX remained on PA12 surface after treatment | 95.28 (stdv.: 5.91) | 92.17 (stdv.: 5.83) |

It can be pointed out that, by using this oleic acid/sodium oleate formulation (40% Oleic Acid/60% Sodium Oleate: coating 5), the Soft and Hard Release Test results at a PTX density of 2.8 μg/mm$^2$ are better or substantially equivalent to the results at a PTX density of 3.5 μg/mm$^2$, but the concentration of PTX was advantageously reduced by 20%. This clearly means that a considerable PTX saving (PTX is a quite expensive drug) can be obtained while still ensuring high performances of the coated balloon in terms of therapeutic agent lost during tracking of the catheter and therapeutic agent available to be released and up-taken by the vessel wall. Analogously, it can be pointed out that, by using the coating solution 5 of the present disclosure, the Soft and Hard Release Test results at a PTX density of 2.1 μg/mm$^2$ are better or substantially equivalent to the results at a PTX density of 3.5 μg/mm$^2$, but the concentration of PTX was advantageously reduced by 40%. Once again, this clearly means that a considerable PTX saving is obtained while still ensuring high performances of the coated balloon in terms of therapeutic agent lost during tracking of the catheter and therapeutic agent available to be released and up-taken by the vessel wall.

The Soft and Hard Release Tests were also carried out on the coating solution 4 at a PTX density of 2.8 μg/mm$^2$ and 2.1 μg/mm$^2$. The results are shown in Tables 4 and 5.

TABLE 4

Coating 4 (PTX density of 2.8 μg/mm$^2$)

| | Soft Release | Hard Release |
|---|---|---|
| % of PTX remained on PA12 surface after treatment | 92.46 (stdv.: 7.39) | 86.72 (stdv.: 6.03) |

TABLE 5

Coating 4 (PTX density of 2.1 μg/mm$^2$)

| | Soft Release | Hard Release |
|---|---|---|
| % of PTX remained on PA12 surface after treatment | 97.66 (stdv.: 7.39) | 92.27 (stdv.: 5.00) |

The comments provided above with reference to coating 5 apply also to coating 4.

Cell Viability Test Results

The In-Vitro Coating Efficacy Evaluation Test and the MTT Test described above were performed on coating solutions of the present disclosure (coatings 4 and 5) as well as on the reference coating in order to evaluate cell viability. Moreover, these tests were carried out on said coating solutions at different PTX densities, in particular at a PTX density of 2.8 µg/mm² and 2.1 µg/mm².

As mentioned above in the in-vitro release test description section, at 72 hours, representative images of cell morphology were obtained. Microscopic observation of the cells demonstrated the efficacy of paclitaxel (PTX) transfer to the cell monolayer, such as lower cell density and larger cell size as compared to the blank controls (i.e. the cells cultured without any contact with the coated samples). In particular, microscopic observation of coatings 4 and 5 of the present disclosure showed that cell death and reduced cell number indicated that a very effective PTX transfer to the cell monolayer occurred.

More in detail, microscopic observation showed that the cellular activity of coating 5 at a PTX density of 3.5 µg/mm² was much greater than the cellular activity of coating 5 at a PTX density of 2.1 µg/mm², the latter being greater than the cellular activity of coating 5 at a PTX density of 2.8 µg/mm², the latter being greater than the cellular activity of coating 4 at a PTX density of 3.5 µg/mm², the latter being substantially equal to the cellular activity of coating 4 at a PTX density of 2.1 µg/mm², the latter being greater than the cellular activity of reference coating 8 at a PTX density of 3.5 µg/mm².

Figure 5:
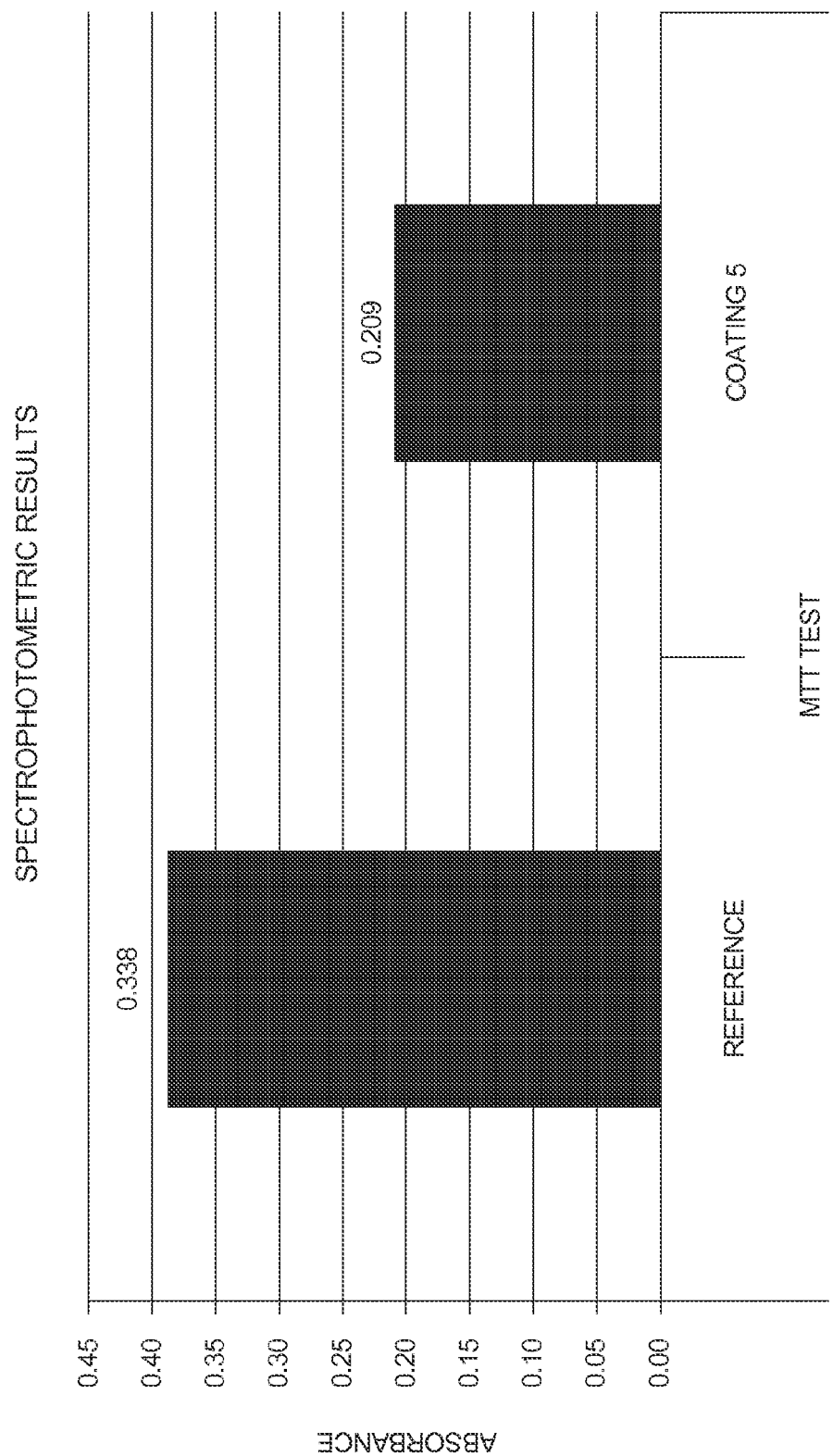
FIG. 5 is a graphical representation of the MTT Test results of a reference coating solution compared with three samples of a coating solution containing 60% sodium oleate and 40% oleic acid coated at a paclitaxel density of 3.5 g/mm$^2$.

The MTT Test results are shown in Tables 6-10 and FIG. 5.

TABLE 6

Coating 5 (PTX density of 3.5 µg/mm²)

| | MTT Test | |
|---|---|---|
| | Coating 8 (reference) | Coating 5 |
| Absorbance | 0.388 | 0.209 |

TABLE 7

Coating 5 (PTX density of 2.8 µg/mm²)

| | MTT Test | |
|---|---|---|
| | Coating 8 (reference) | Coating 5 |
| Absorbance | 0.388 (stdv. = 0.028) | 0.317 (stdv. = 0.018) |

TABLE 8

Coating 5 (PTX density of 2.1 µg/mm²)

| | MTT Test | |
|---|---|---|
| | Coating 8 (reference) | Coating 5 |
| Absorbance | 0.388 (stdv. = 0.028) | 0.302 (stdv. = 0.113) |

TABLE 9

Coating 4 (PTX density of 3.5 µg/mm²)

| | MTT Test | |
|---|---|---|
| | Coating 8 (reference) | Coating 4 |
| Absorbance | 0.388 (stdv. = 0.028) | 0.357 (stdv. = 0.095) |

TABLE 10

Coating 4 (PTX density of 2.1 µg/mm²)

| | MTT Test | |
|---|---|---|
| | Coating 8 (reference) | Coating 4 |
| Adsorbence | 0.388 (stdv. = 0.028) | 0.355 (stdv. = 0.092) |

Figure 6:
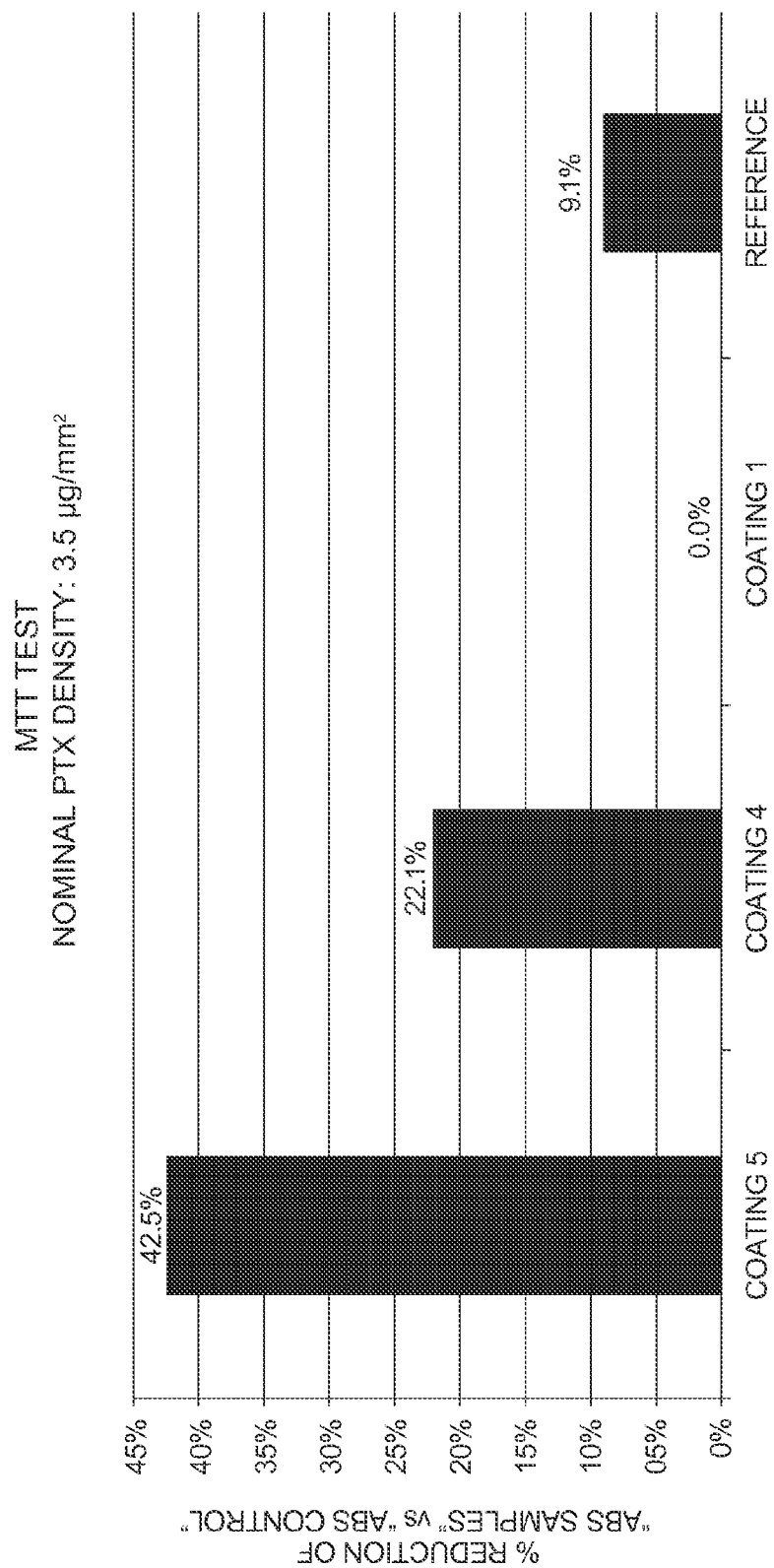
FIG. 6 is a graphical representation of the MTT Test results for various ratios of oleic acid/sodium oleate at a constant PTX coating density of 3.5 µg/mm$^2$.

A comparison of the MTT Test results for the various ratios of sodium oleate and oleic acid at a constant PTX density of 3.5 µg/mm² is shown in FIG. 6 (relative to the reference coating and to coating 1). These results indicate that the absorbance of the coatings of the present disclosure is remarkably lower than the absorbance of the reference solution, and thus the coatings of the present disclosure have higher efficacy than the reference coating (i.e. the cell proliferation is considerably prevented with the coatings of the present disclosure).

Figure 7:
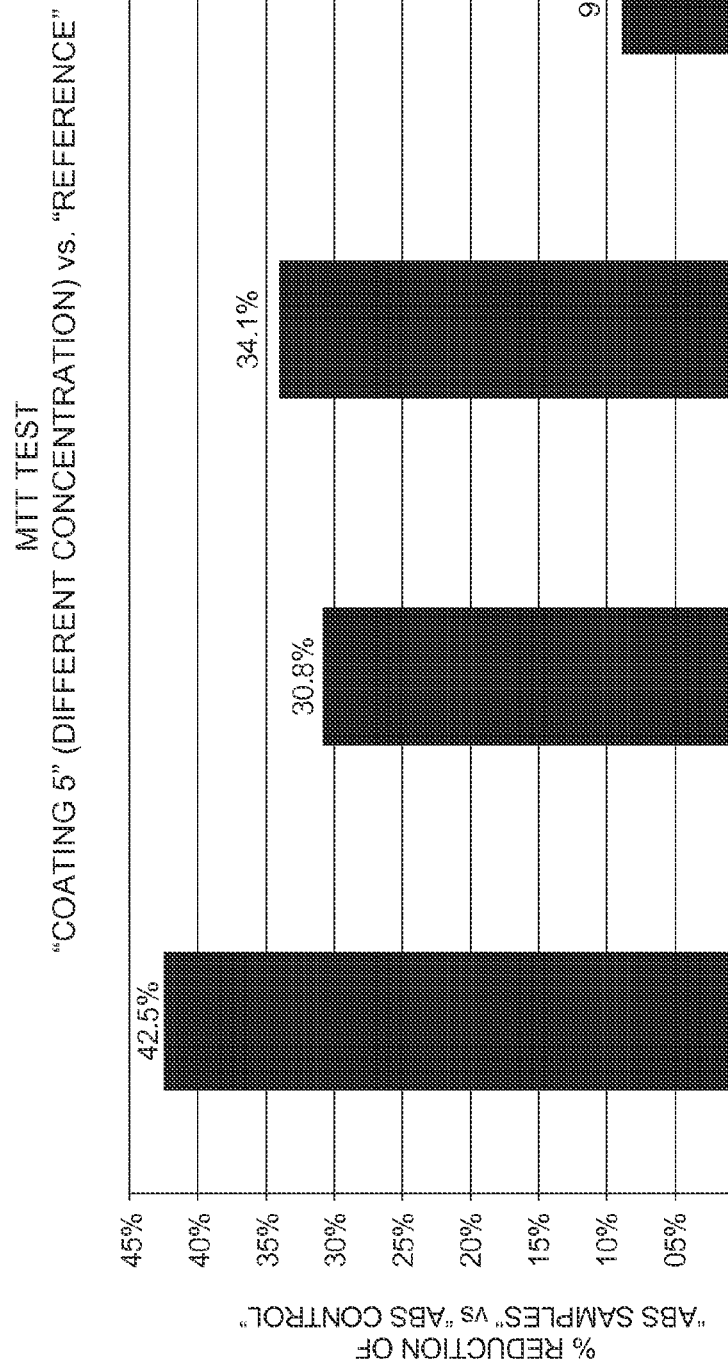
FIG. 7 is a graphical representation of the MTT Test results for a ratio of 60% sodium oleate/40% oleic acid at various PTX coating densities of 3.5, 2.8, and 2.1 µg/mm$^2$.

A comparison of the MTT Test results for a ratio of 40% oleic acid/60% sodium oleate at various PTX densities, respectively of 3.5, 2.8, and 2.1 µg/mm², is shown in FIG. 7 (relative to the reference coating). These results indicate that the coating efficacy (in terms of prevention of cell membrane proliferation) of the present disclosure is remarkably higher than that of the reference coating, even at a lower therapeutic agent density. In fact, the coating 5 at a therapeutic agent density of 2.1 µg/mm² has a reduction of the absorbance percentage considerably higher than the reference coating at a therapeutic agent density of 3.5 µg/mm². This result is particularly important because it shows that the coating of the present disclosure allows for a great (and better) result (in terms of efficacy of the cell membrane proliferation reduction) even at a sensibly lower therapeutic agent concentration. It is apparent that, if a lower amount of therapeutic agent can be used, the safety of the medical device is improved (since less therapeutic agent is introduced into the human body and, in particular, the risk of therapeutic agent particulate being released from the balloon surface is reduced) and some money can be advantageously saved too (since the therapeutic agent may be quite expensive).

Figure 8:
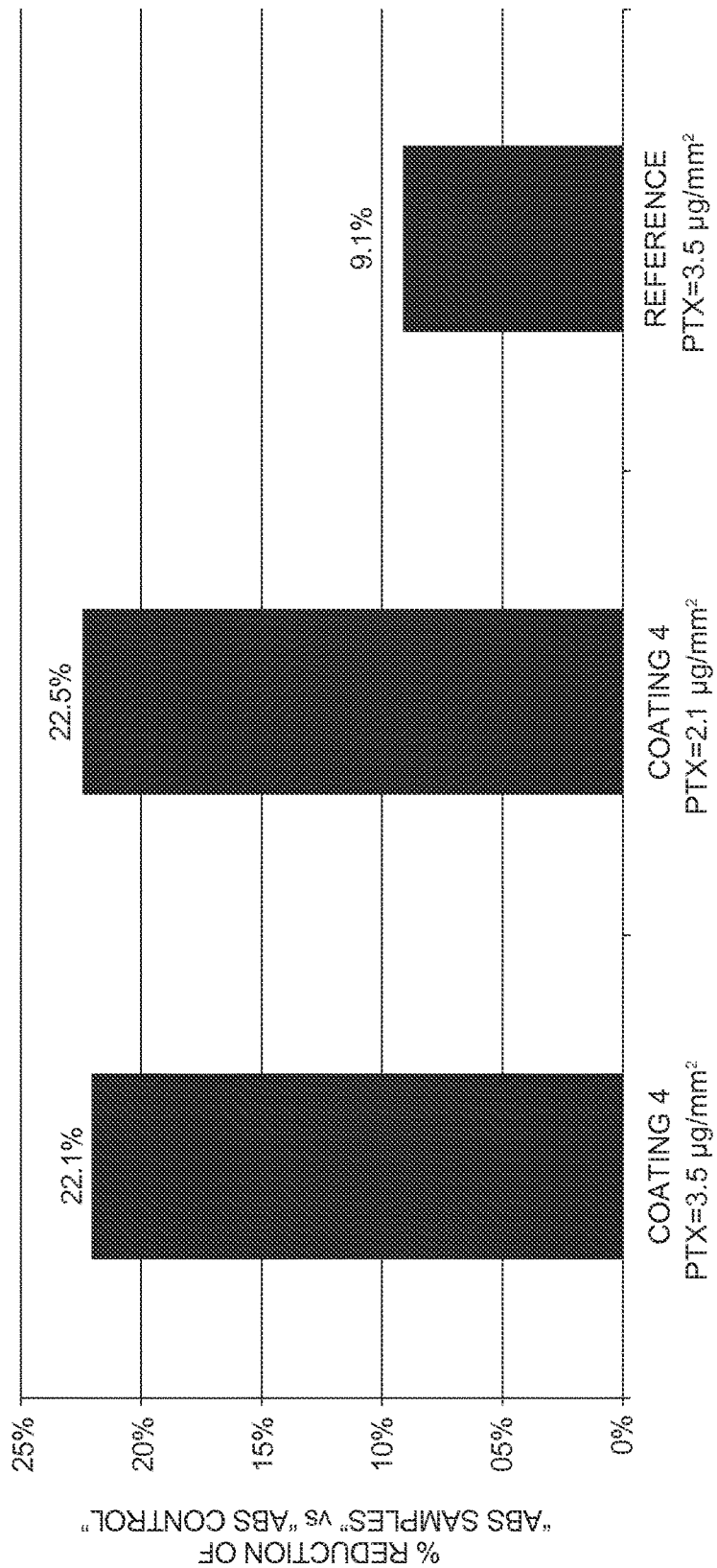
FIG. 8 is a graphical representation of the MTT Test results for a ratio of 50% sodium oleate/50% oleic acid at PTX coating densities of 3.5 and 2.1 µg/mm$^2$.

A comparison of the MTT Test results for a ratio of 50% oleic acid/50% sodium oleate at various PTX densities of 3.5 and 2.1 µg/mm² is shown in FIG. 8 (relative to the reference coating). The same considerations done for FIG. 7 apply also to FIG. 8 and thus to the coating 4 of the present disclosure.

CONCLUSIONS

Surprisingly, comparing with reference coating, the formulations of the present disclosure provide higher performance in release simulation tests (Hard and Soft Release Tests). Moreover, in vitro simulation treatment and the microscopic analysis showed increased paclitaxel efficacy in terms of cell death relative to the reference coating.

The coating efficiency with the oleate-based excipient at a PTX density of 2.1 µg/mm² remained higher than the reference coating at a PTX density of 3.5 µg/mm².

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed:

1. A coated medical balloon comprising a polymeric material having a surface with a therapeutic agent-containing mixture coated thereon, wherein the mixture comprises a therapeutic agent, an unsaturated carboxylic acid, an alkali metal salt of the unsaturated carboxylic acid, and an optional excipient; and further wherein the unsaturated carboxylic acid is selected from the group of fatty acids having a (C6-C20) carbon chain with a single cis C=C bond.

2. The balloon of claim 1 wherein the unsaturated carboxylic acid is oleic acid.

3. The balloon of claim 1 wherein the alkali metal salt is a sodium salt.

4. The balloon of claim 1 wherein the ratio of acid to salt is within a range of 80:20 to 20:80.

5. The balloon of claim 4 wherein the ratio of acid to salt is within a range of 60:40 to 40:60.

6. The balloon of claim 1 wherein the therapeutic agent is a Taxane.

7. The balloon of claim 6 wherein the Taxane is paclitaxel.

8. The balloon of claim 1 wherein the therapeutic agent-containing mixture further comprises an excipient.

9. The balloon of claim 8 wherein the excipient is selected from ascorbic acid, urea, polyethylene glycol, and a triglyceride.

10. A coated medical balloon comprising a surface having a therapeutic agent-containing mixture coated thereon, wherein the mixture comprises a therapeutic agent, an unsaturated carboxylic acid, a salt of the unsaturated carboxylic acid, and an optional excipient, wherein the ratio of acid to salt is within a range of 60:40 to 40:60.

11. A coated medical balloon comprising a surface having a therapeutic agent-containing mixture coated thereon, wherein the mixture comprises a therapeutic agent, an unsaturated carboxylic acid, a salt of the unsaturated carboxylic acid, and an optional excipient, wherein the ratio of acid to salt is within a range of 60:40 to 40:60; and further wherein the unsaturated carboxylic acid is selected from the group of fatty acids having a (C6-C20) carbon chain with a single cis C=C bond.

12. The balloon of claim 11 wherein the unsaturated carboxylic acid is oleic acid.

13. The balloon of claim 11 wherein the salt is an alkali metal salt.

14. The balloon of claim 13 wherein the alkali metal salt is a sodium salt.

15. The balloon of claim 11 wherein the therapeutic agent is a Taxane.

16. The balloon of claim 15 wherein the Taxane is paclitaxel.

17. The balloon of claim 11 wherein the therapeutic agent-containing mixture further comprises an excipient.

18. The balloon of claim 17 wherein the excipient is selected from ascorbic acid, urea, polyethylene glycol, and a triglyceride.

19. A balloon catheter comprising:
an elongated catheter shaft having proximal and distal ends, wherein the catheter shaft defines a longitudinal axis extending between the proximal and distal ends; and
an inflatable balloon located close to the distal end of the catheter shaft, wherein the balloon comprises a polymeric material having a surface with a therapeutic agent-containing mixture coated thereon, wherein the mixture comprises a therapeutic agent, an unsaturated carboxylic acid, an alkali metal salt of the unsaturated carboxylic acid, and an optional excipient; and further wherein the unsaturated carboxylic acid is selected from the group of fatty acids having a (C6-C20) carbon chain with a single cis C=C bond.

20. A balloon catheter comprising:
an elongated catheter shaft having proximal and distal ends, wherein the catheter shaft defines a longitudinal axis extending between the proximal and distal ends; and
an inflatable balloon located close to the distal end of the catheter shaft, wherein the balloon comprises a polymeric material having a surface with a therapeutic agent-containing mixture coated thereon, wherein the mixture comprises a therapeutic agent, an unsaturated carboxylic acid, a salt of the unsaturated carboxylic acid, and an optional excipient, wherein the ratio of acid to salt is within a range of 60:40 to 40:60; and further wherein the unsaturated carboxylic acid is selected from the group of fatty acids having a (C6-C20) carbon chain with a single cis C=C bond.

21. A method of delivering a therapeutic agent to a diseased vessel, the method comprising:
providing a balloon catheter of claim 19;
advancing the balloon catheter into the diseased vessel; and
inflating the inflatable balloon to form an inflated balloon that contacts the wall of the diseased vessel and thereby delivers the therapeutic agent from the surface of the inflated balloon to the diseased vessel.

22. A method of delivering a therapeutic agent to a diseased vessel, the method comprising:
providing a balloon catheter of claim 20;
advancing the balloon catheter into the diseased vessel; and
inflating the inflatable balloon to form an inflated balloon that contacts the wall of the diseased vessel and thereby delivers the therapeutic agent from the surface of the inflated balloon to the diseased vessel.

23. A method of reducing the amount of therapeutic agent on a coated balloon, the method comprising:
providing a medical balloon comprising a polymeric material having a surface;
combining components comprising a therapeutic agent, an unsaturated carboxylic acid, a salt of the unsaturated carboxylic acid, and an optional excipient to form a mixture; wherein the unsaturated carboxylic acid is selected from the group of fatty acids having a (C6-C20) carbon chain with a single cis C=C bond; and
coating the mixture onto the surface of the medical balloon.

24. A method of reducing the amount of therapeutic agent on a coated balloon, the method comprising:

providing a medical balloon having a surface;

combining components comprising a therapeutic agent, an oleic acid, an alkali metal salt of the oleic acid, and an optional excipient to form a mixture, wherein the ratio of acid to salt is within a range of 80:20 to 20:80; and further wherein the unsaturated carboxylic acid is selected from the group of fatty acids having a (C6-C20) carbon chain with a single cis C=C bond; and coating the mixture onto the surface of the medical balloon.

* * * * *